US00PP31523P2

(12) United States Plant Patent
Pierron-Darbonne

(10) Patent No.: US PP31,523 P2
(45) Date of Patent: Mar. 10, 2020

(54) BLUEBERRY PLANT NAMED 'PLABLUE 1525'

(50) Latin Name: ***Vaccinium Corymbosum* L.**
Varietal Denomination: Plablue 1525

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal, Valtierra, Navarra (ES)

( * ) Notice: Subject to any disclaimer, the term of this patent is extended or adjusted under 35 U.S.C. 154(b) by 0 days.

(21) Appl. No.: 16/501,256

(22) Filed: Mar. 13, 2019

(30) Foreign Application Priority Data

Aug. 9, 2018 (QZ) ..... PBR 2018/2070

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — Knobbe, Martens, Olson & Bear, LLP

(57) ABSTRACT

Descried herein is a new and distinct blueberry variety with varietal denomination 'Plablue 1525', characterized by a combination of traits which include, a semi upright plant growth habit, and very abundant production of large fruit-size, oblate shaped and firm fruit. 'Plablue 1525' is a self-fertile variety.

17 Drawing Sheets

Botanical classification: *Vaccinium corymbosum* L.

Variety denomination: The new plant has the varietal denomination 'Plablue 1525'.

CROSS-REFERENCE TO RELATED APPLICATIONS

This application claims the benefit of European Community Plant Variety Office Application No. 2018/2070, for a blueberry variety named 'Plablue 1525,' filed on Aug. 9, 2018, the entirety of which is incorporated by reference herein.

BACKGROUND

Disclosed herein is a new and distinct southern highbush blueberry variety (*Vaccinium corymbosum* L.). The new variety of blueberry was created in a breeding program by crossing two parents; in particular, by crossing as seed parent an undistributed blueberry parent designated 14.01.001 (unpatented) and as pollen parent an undistributed blueberry parent designated 14.08.001 (unpatented). Female and male are selections from breeder's program. Both parental varieties are property and have not been commercialized.

The new variety was grown and asexually propagated by softwood cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between about November 20 and June 22 of the following year.

SUMMARY

The present invention relates to a new and distinct southern highbush blueberry variety. The varietal denomination of the new variety is 'Plablue 1525', that produces and maintains a medium vigorous plant with consistent fruit production from beginning March through ending May. Among the characteristics which appear to distinguish the new variety from other varieties are a combination of traits which include a semi upright plant growth habit, and very abundant production of large fruit-size, oblate shaped and firm fruit.

The new blueberry plant variety 'Plablue 1525' has not been observed under all possible environmental conditions. The phenotype may vary somewhat with variations in environmental and cultural practices such as temperature and light intensity without, however, any variance in genotype.

COMPARISON TO THE PARENTS

The seed and pollen parents were both obtained by Plantaqs de Navarra, S.A. Sociedad Unipersonal. They are selections from the breeder's program of Plantas de Navarra, S.A. Sociedad Unipersonal. They are property of Plantas de Navarra, S.A. Sociedad Unipersonal. Plantas de Navarra, S.A. Sociedad Unipersonal maintains them in their nursery.

The new variety is distinguished from its parents by the following characteristics possessed by 'Plablue 1525' which are different than, or not possessed, by the seed parent designated '14.01.001' (unpatented) and the pollen parent designated '14.08.001' (unpatented).

Leaf shape of the seed parent '14.01.001' (unpatented) is elliptic, whereas leaf shape of 'Plablue 1525' is lanceolate.

Diameter of calyx basin of fruit of the seed parent '14.01.001' (unpatented) shows a medium size, whereas diameter of calyx basin of fruit of 'Plablue 1525' shows a large size.

Length of internode on one-year-old shoot of the pollen parent '14.08.001' (unpatented) is short, whereas length of internode on one-year-old shoot of 'Plablue 1525' is medium.

Depth of the calyx basin of fruit of the pollen parent '14.08.001' (unpatented) is medium, whereas depth of the calyx basin of fruit of 'Plablue 1525' is shallow.

COMPARISON TO CLOSEST VARIETY

The new variety is closest to the variety 'Legacy' (unpatented), but is distinguished therefrom by the following characteristics possessed by 'Plablue 1525' which are different than, or not possessed by 'Legacy'.

The plant of 'Legacy' (unpatented) exhibits a weak vigor, whereas the plant of 'Plablue 1525' exhibits a medium vigor.

Length of leaf of 'Legacy' (unpatented) is shorter than length of leaf of 'Plablue 1525'.

Length of inflorescence of 'Legacy' (unpatented) is longer than length of inflorescence of 'Plablue 1525'.

Density of fruit cluster of 'Legacy' (unpatented) is higher than density of fruit cluster of 'Plablue 1525'.

'Legacy' (unpatented) shows a fruit size smaller than 'Plablue 1525'.

Depth of calyx basin in the fruit of 'Legacy' (unpatented) is medium, whereas depth of calyx in the fruit of 'Plablue 1525' is shallow.

Fruit of 'Legacy' is more firm than fruit of 'Plablue 1525'

Time of beginning of fruit ripening on one-year-old shoot of 'Legacy' (unpatented) is less early than in 'Plablue 1525'.

Differences in vigor of 'Plablue 1525' (designated 15.07.005) and 'Legacy' (unpatented) are shown in FIG. 1 and FIG. 13. Differences in length of leaf of 'Plablue 1525' (designated 15.07.005) and 'Legacy' (unpatented) are shown in FIG. 3 and FIG. 14. Differences in density of fruit cluster of 'Plablue 1525' (designated 15.07.005) and 'Legacy' (unpatented) are shown in FIG. 8 and FIG. 15. Differences in fruit size of 'Plablue 1525' (designated 15.07.005) and 'Legacy' (unpatented) are shown in FIG. 9 and FIG. 16. Differences in depth of calyx basin in the fruit of 'Plablue 1525' (designated 15.07.005) and the fruit of 'Legacy' (unpatented) are shown in FIG. 10 and FIG. 17. These differences are maintained during the harvest season.

BRIEF DESCRIPTION OF THE ILLUSTRATIONS

The accompanying photographs show typical specimens of the new variety, designated 15.07.005 in the illustrations, including fruit, foliage and flower, in color as nearly true as it is reasonably possible to make in color illustrations of this character.

The plants depicted in the drawings were planted October 14 in the farm in Cartaya (Huelva), Spain, about 7° W, 37° N, 45 feet elevation.

Drawings/photographs were taken in April (about April 4 and April 12): minimum temperate about 11° to 12° Centigrade, maximum temperate about 25 to 26° Centigrade.

FIG. 1 and FIG. 2 shows several plants of the new variety (designated 15.07.005) which exhibit a semi upright habit plant with several clusters of violet-blue color fruit (RHS Violet-Blue group color near 97 C to 97 D) with wax and oblated shape fruits.

FIG. 3 and FIG. 4 show the upper side and the underside, respectively, of a complete leave of the new variety (designated 15.07.005). In it, we can see that the leaf color of upper side of the new variety (designated 15.07.005) is a green color (RHS Green group near 139 B to 139 A) and the leaf color of underside of the new variety (designated 15.07.005) is a green color (RHS Green group color near 138 C to 138 B).

FIG. 5 shows an immature flower of the new variety (designated 15.07.005). In it, we can see the immature flower yellow-green color (RHS Yellow-Green group color near 145 D to 145 C).

FIG. 6 shows a typical flower of the new variety (designated 15.07.005). In it, we can see the corolla of the new variety (designated 15.07.005) with white color (RHS White group color near 155 B to 155 A).

DESCRIPTION OF THE NEW VARIETY

Figure 1:
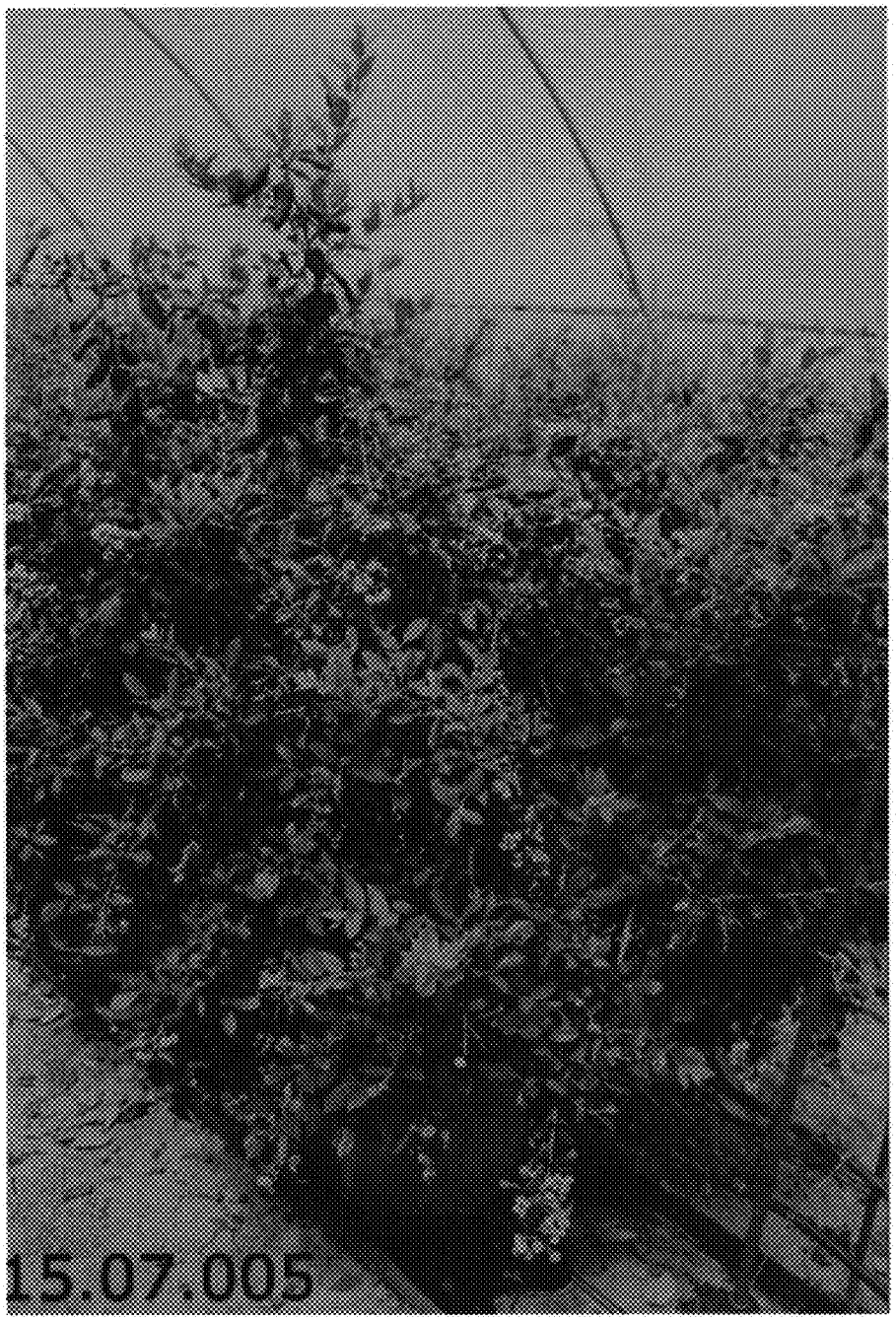
Figure 2:
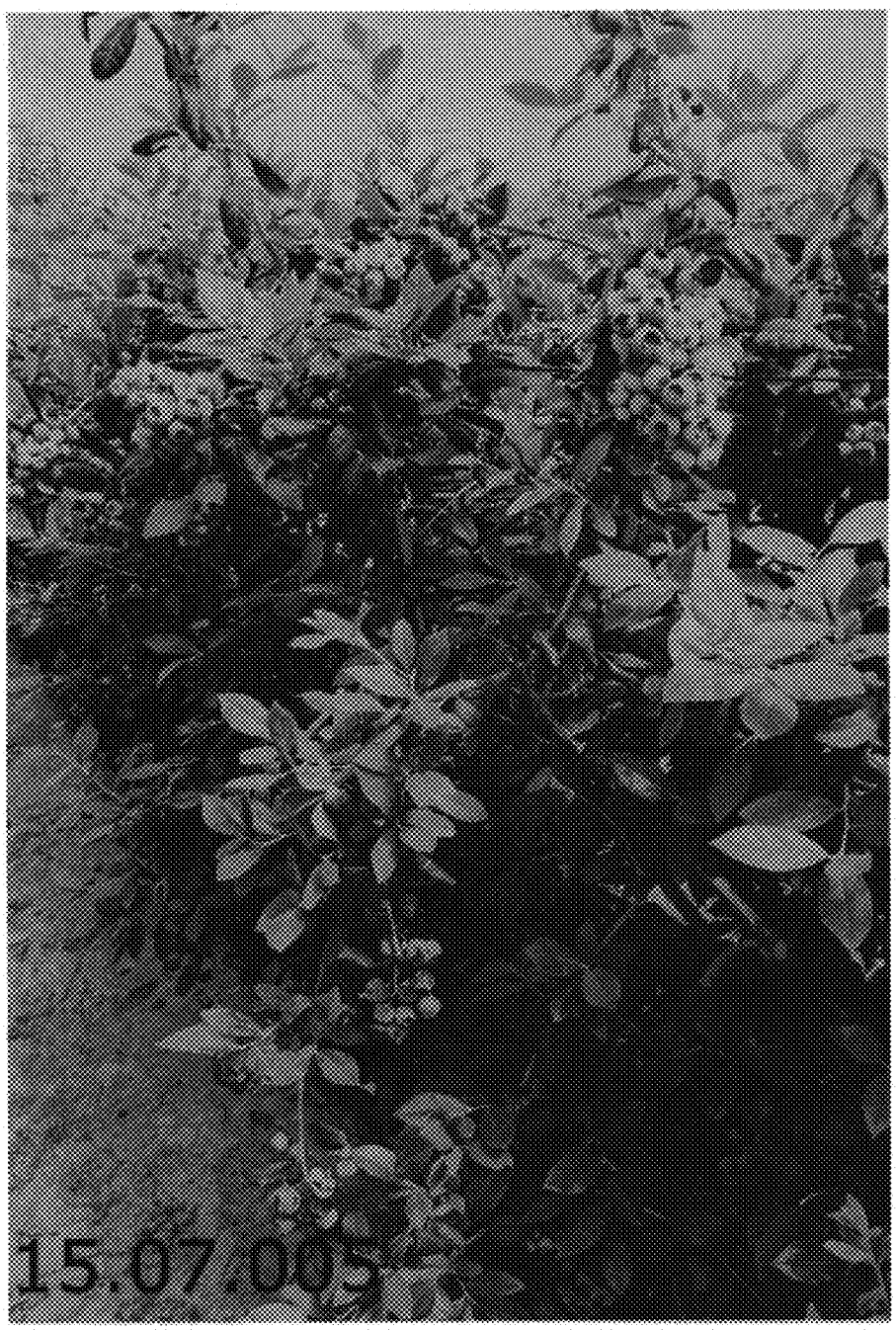
Figure 3:
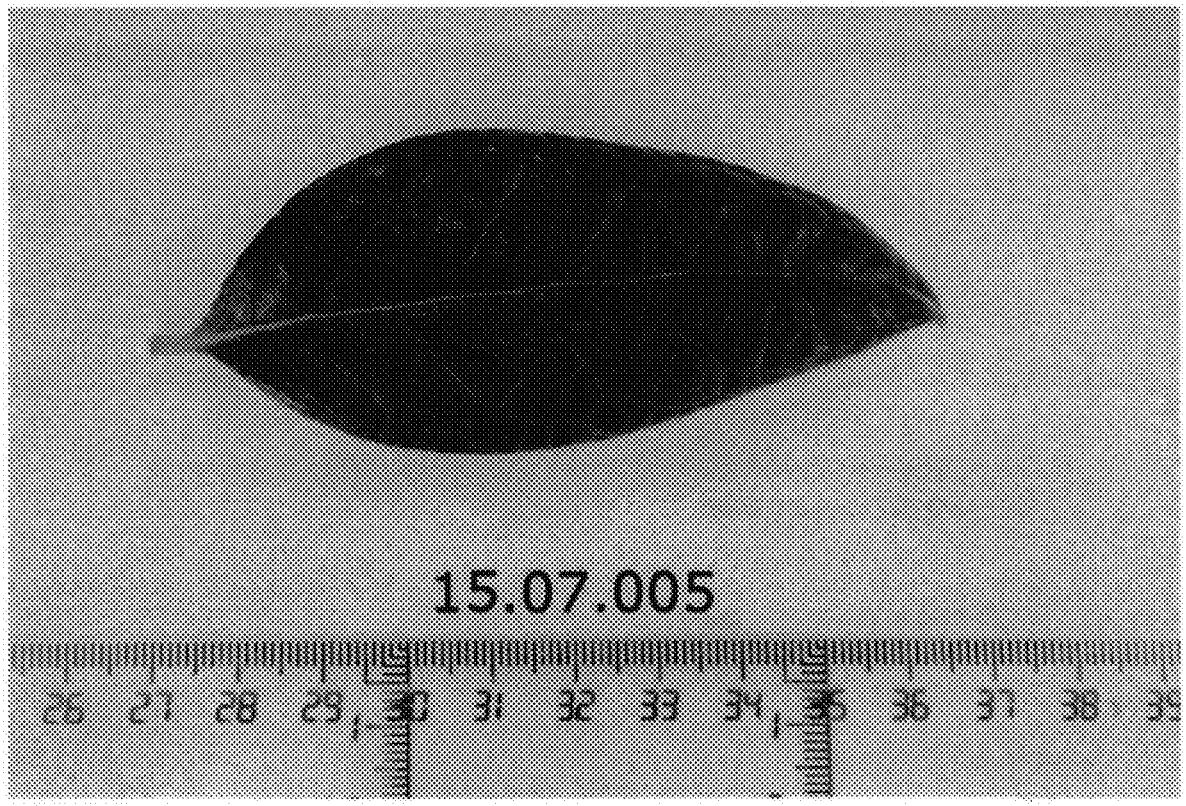
Figure 4:
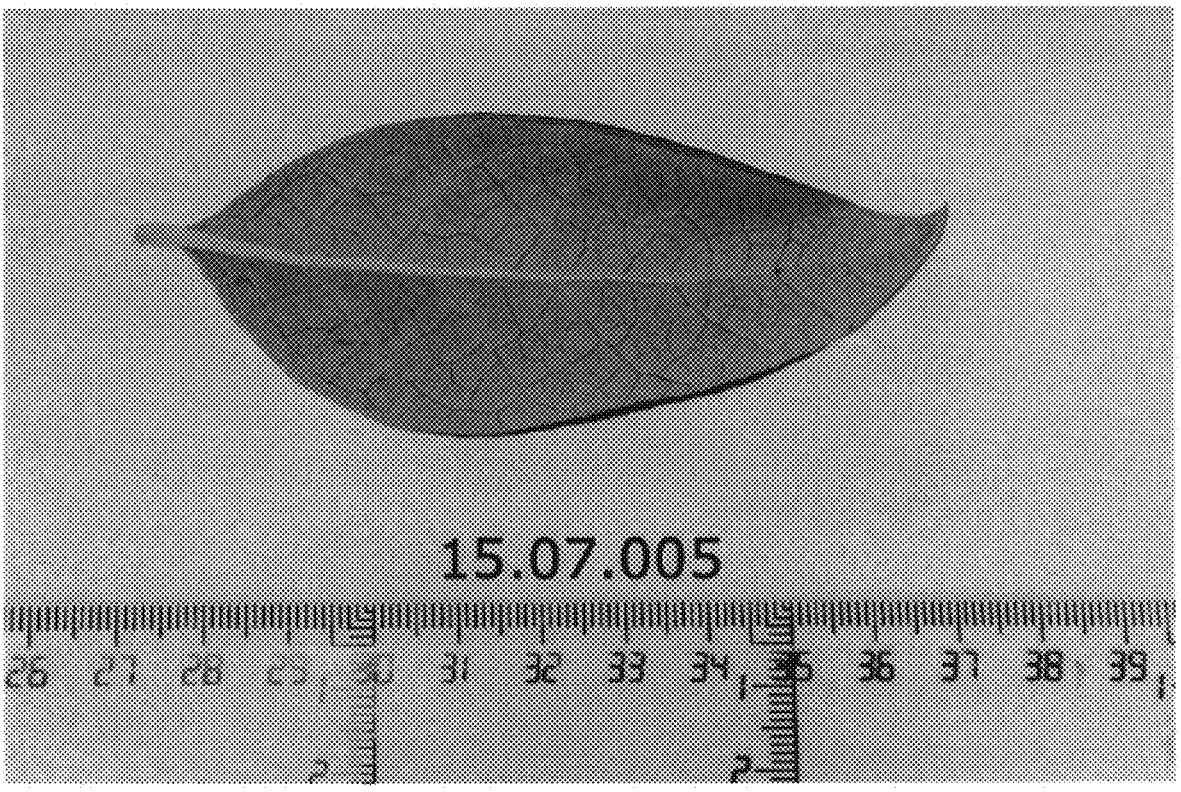
Figure 5:
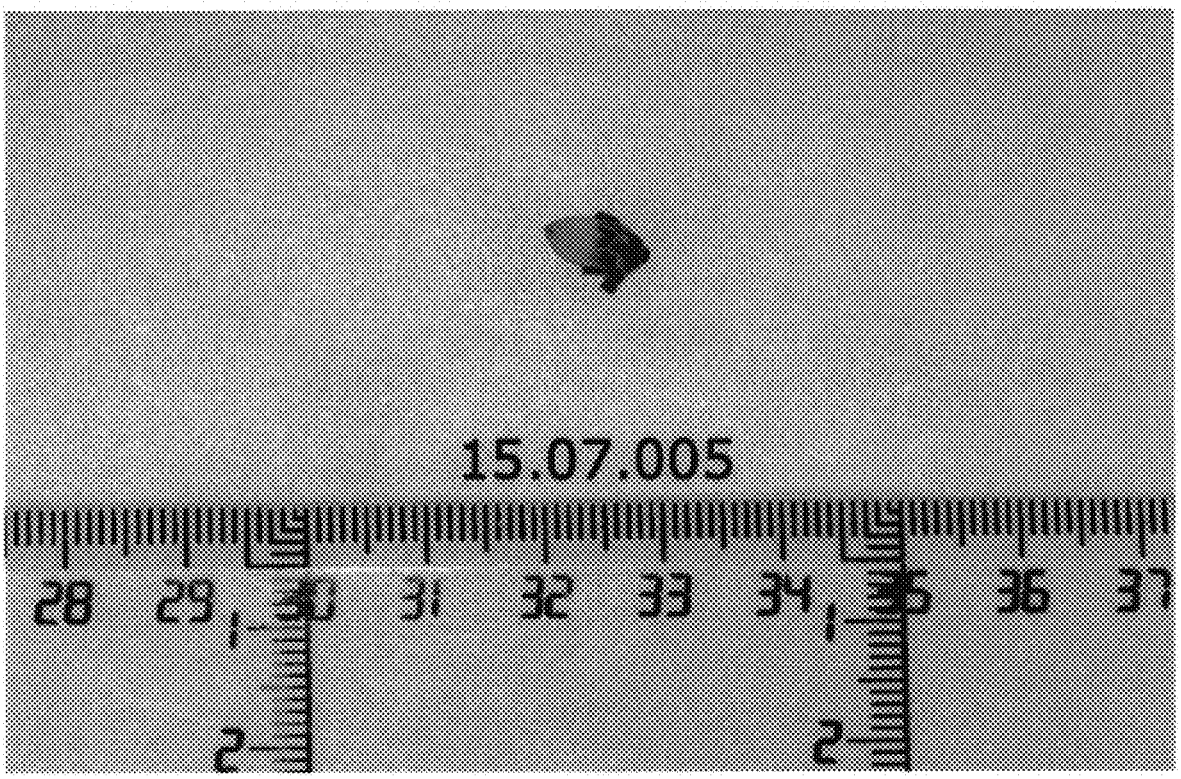
Figure 6:
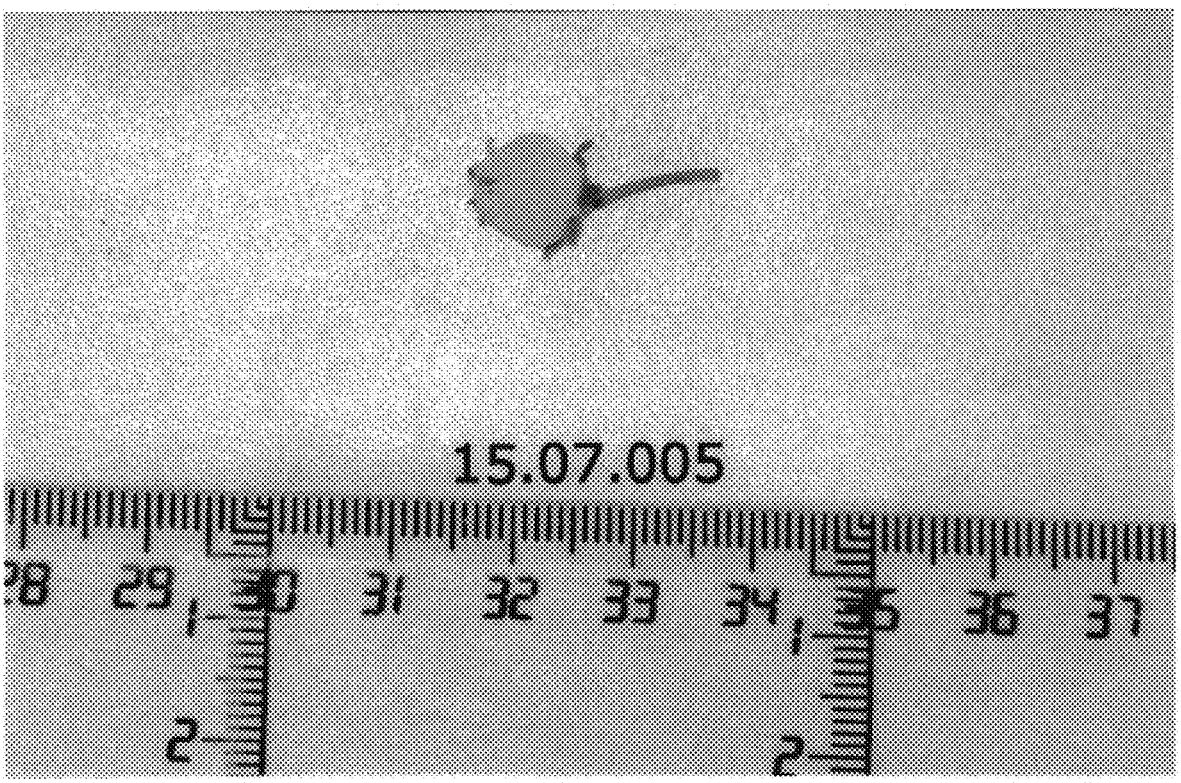
Figure 7:
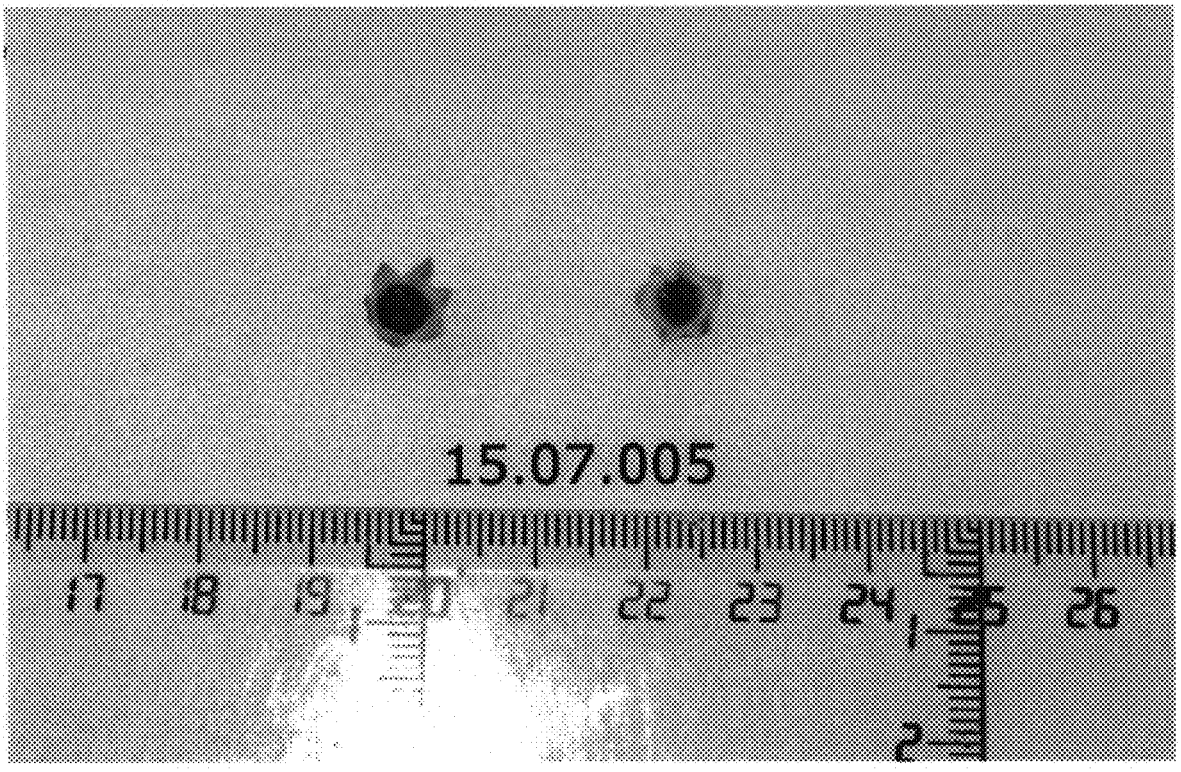
FIG. 7 shows typical sepals of the new variety (designated 15.07.005) with Yellow-Green color (RHS Yellow-Green group color near 144 D to 144 C).
Figure 8:
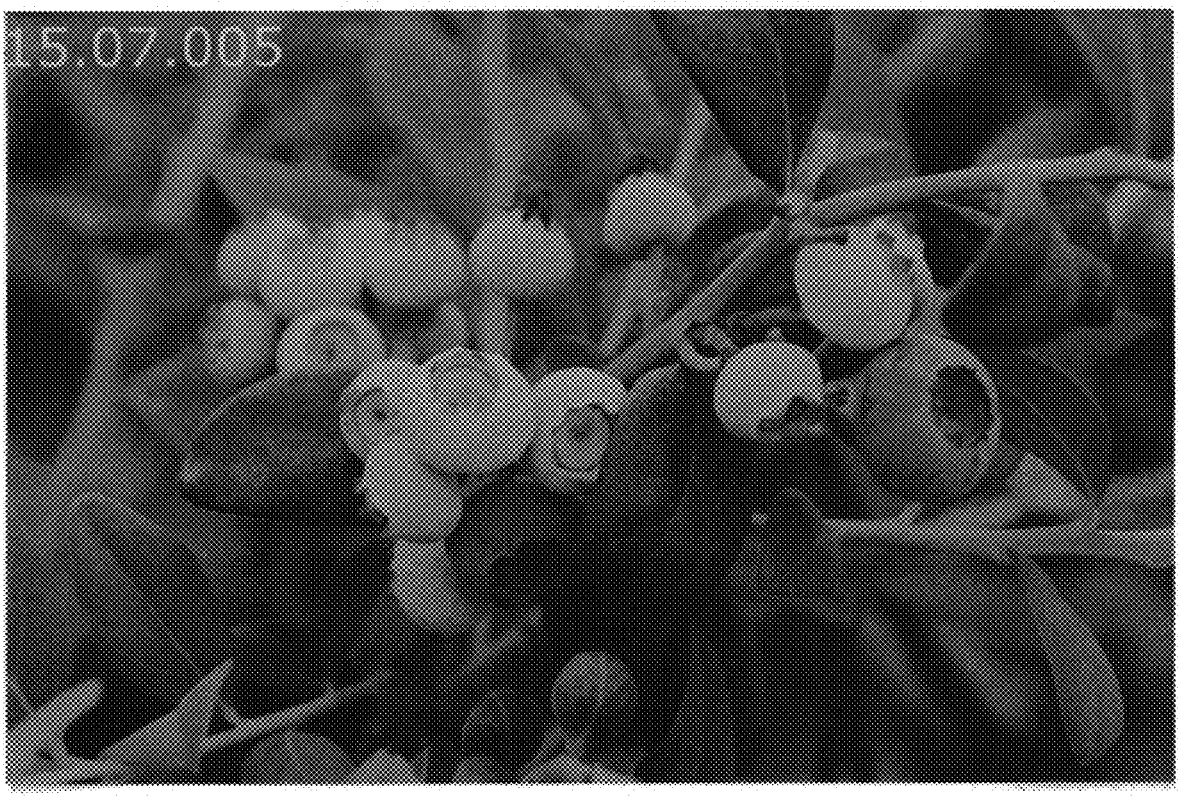
FIG. 8 shows the density of fruit cluster of the new variety (designated 15.07.005).
Figure 9:
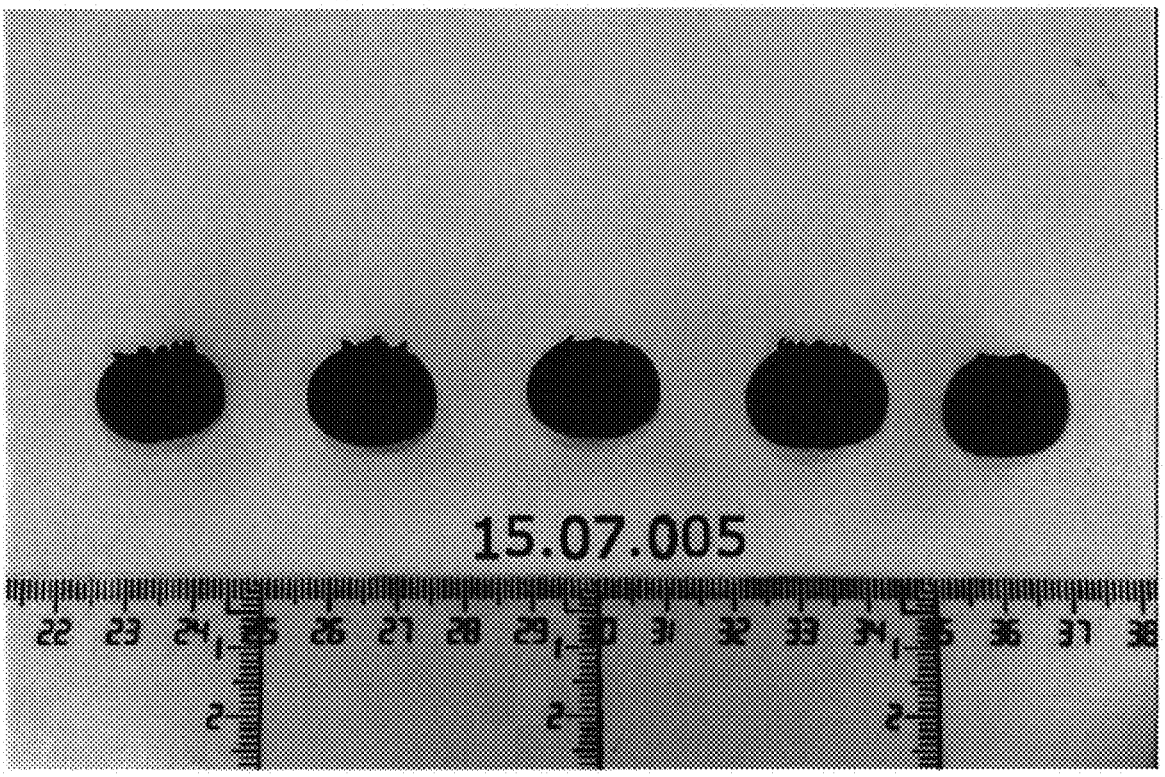
FIG. 9 and FIG. 10 show typical fruits of the new variety (designated 15.07.005) with oblate shape and violet-blue color with wax (RHS Violet-Blue group color near 97 C to 97 D).
Figure 10:
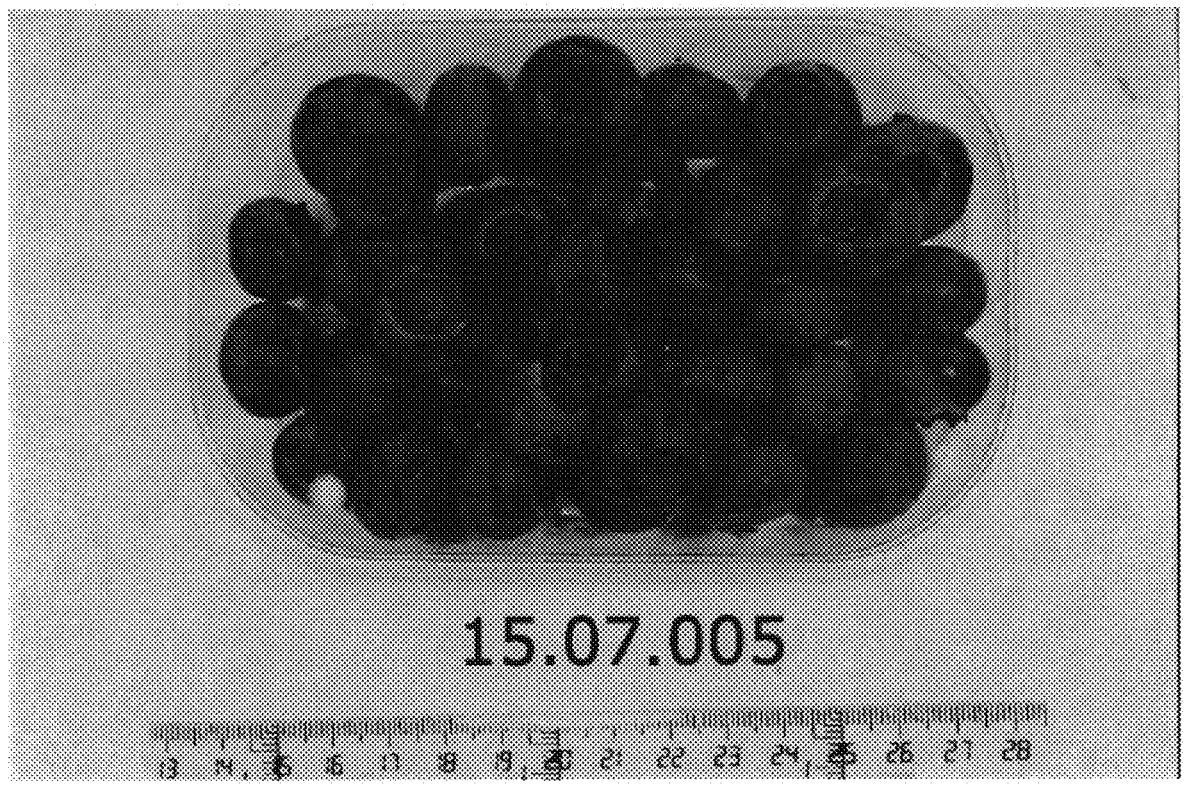
Figure 11:
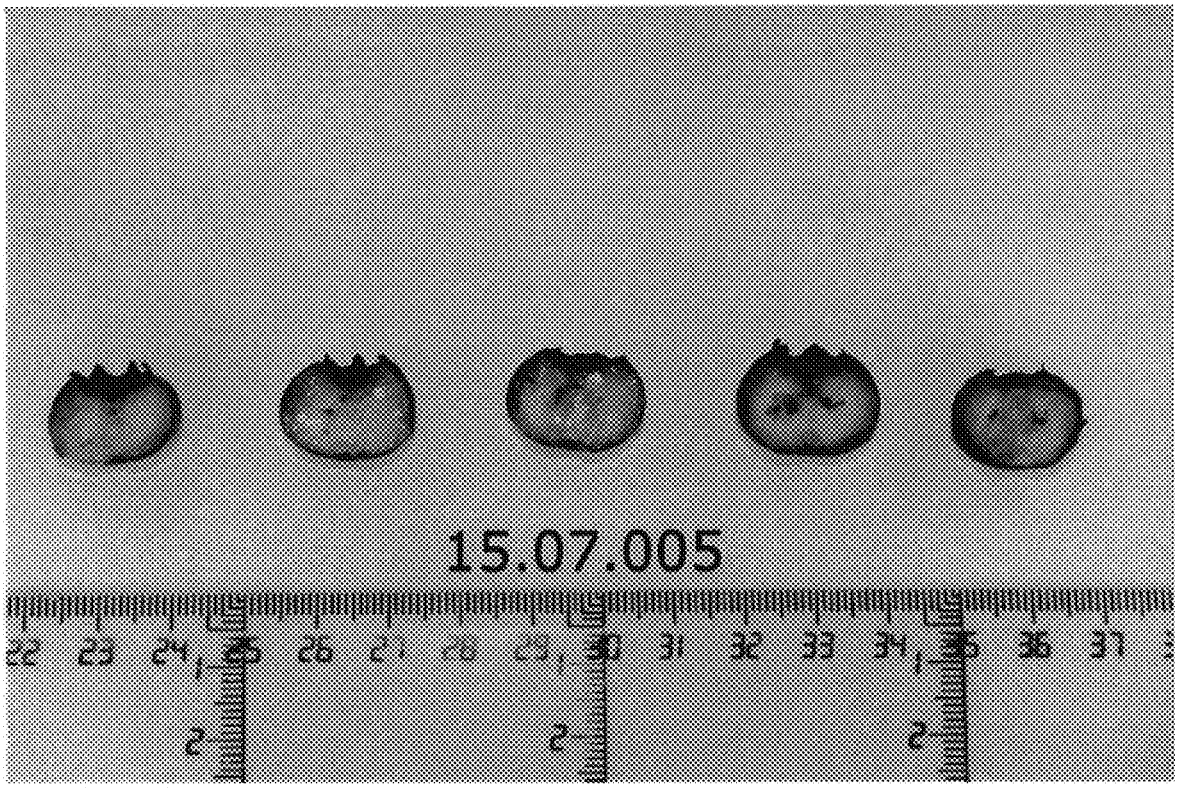
FIG. 11 shows typical sliced fruits of the new variety (designated 15.07.005) with yellow-green flesh color (RHS Yellow-Green group color near 149 D to 150 D).
Figure 12:
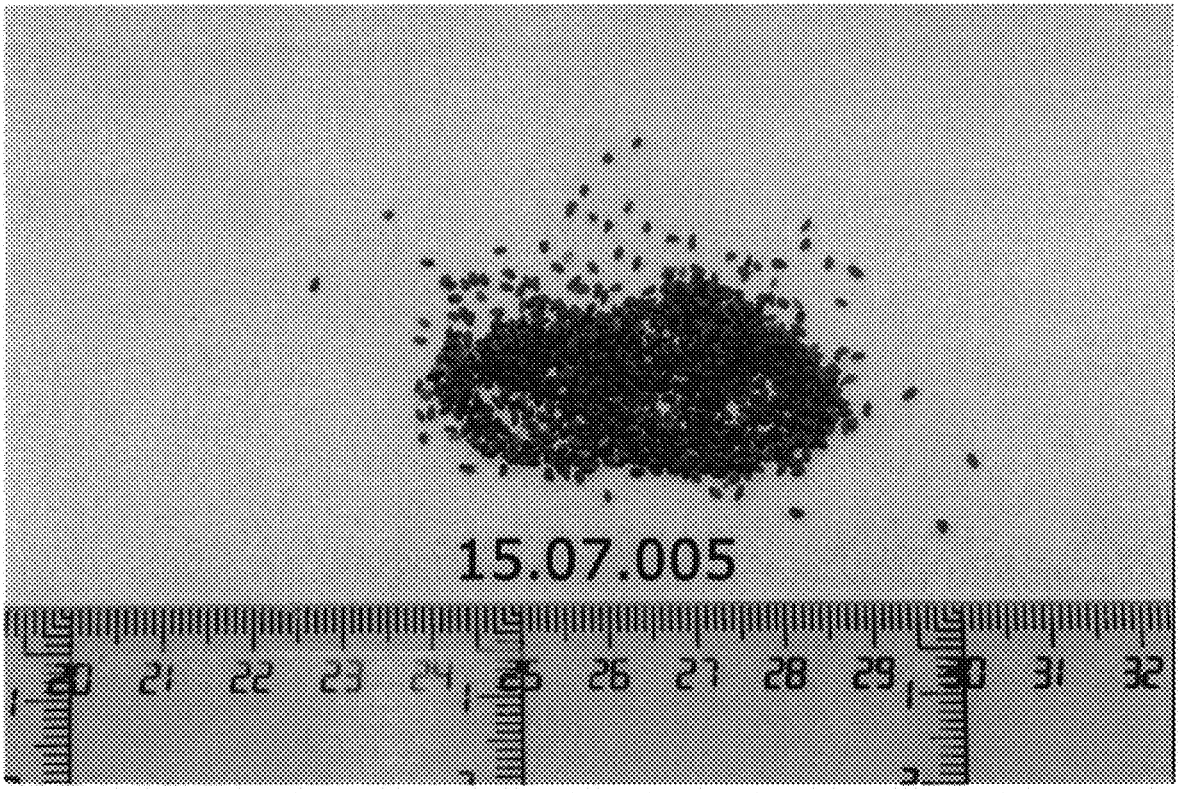
FIG. 12 shows typical seeds of the new variety (designated 15.07.005) with greyed-orange color (RHS Greyed-Orange group color near 165 B to 165 A).
Figure 13:
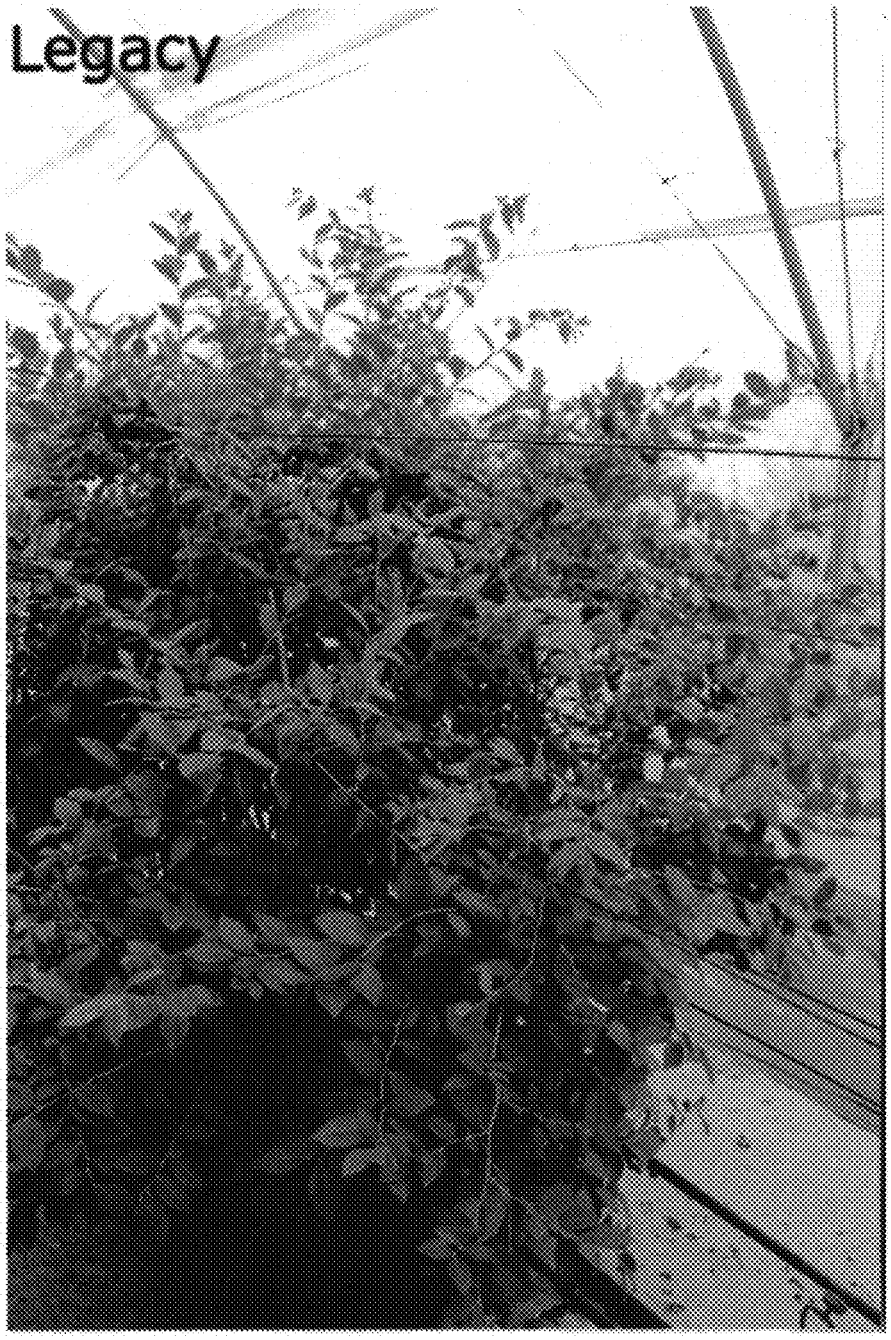
FIG. 13 shows several plants of the blueberry variety 'Legacy' (unpatented) which exhibits a weak vigor.
Figure 14:
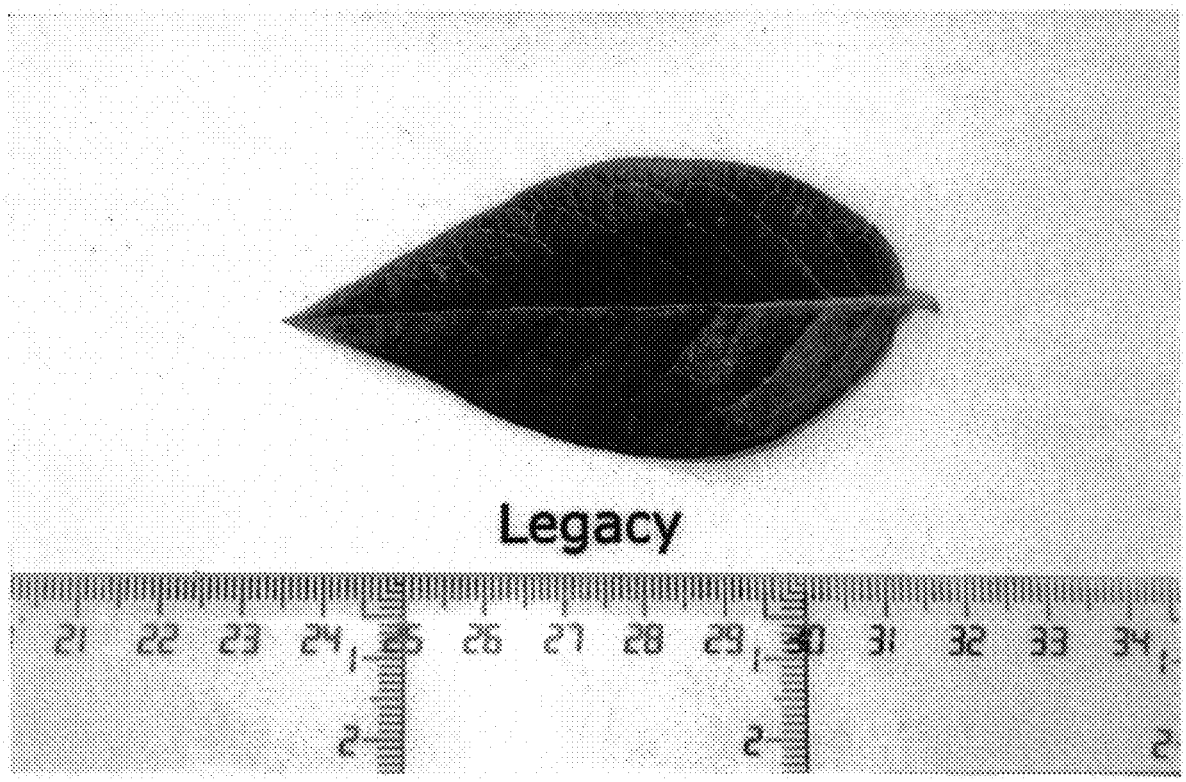
FIG. 14 shows the leaf of blueberry variety 'Legacy' (unpatented) shorter than leaf of the new variety (designated 15.07.005).
Figure 15:
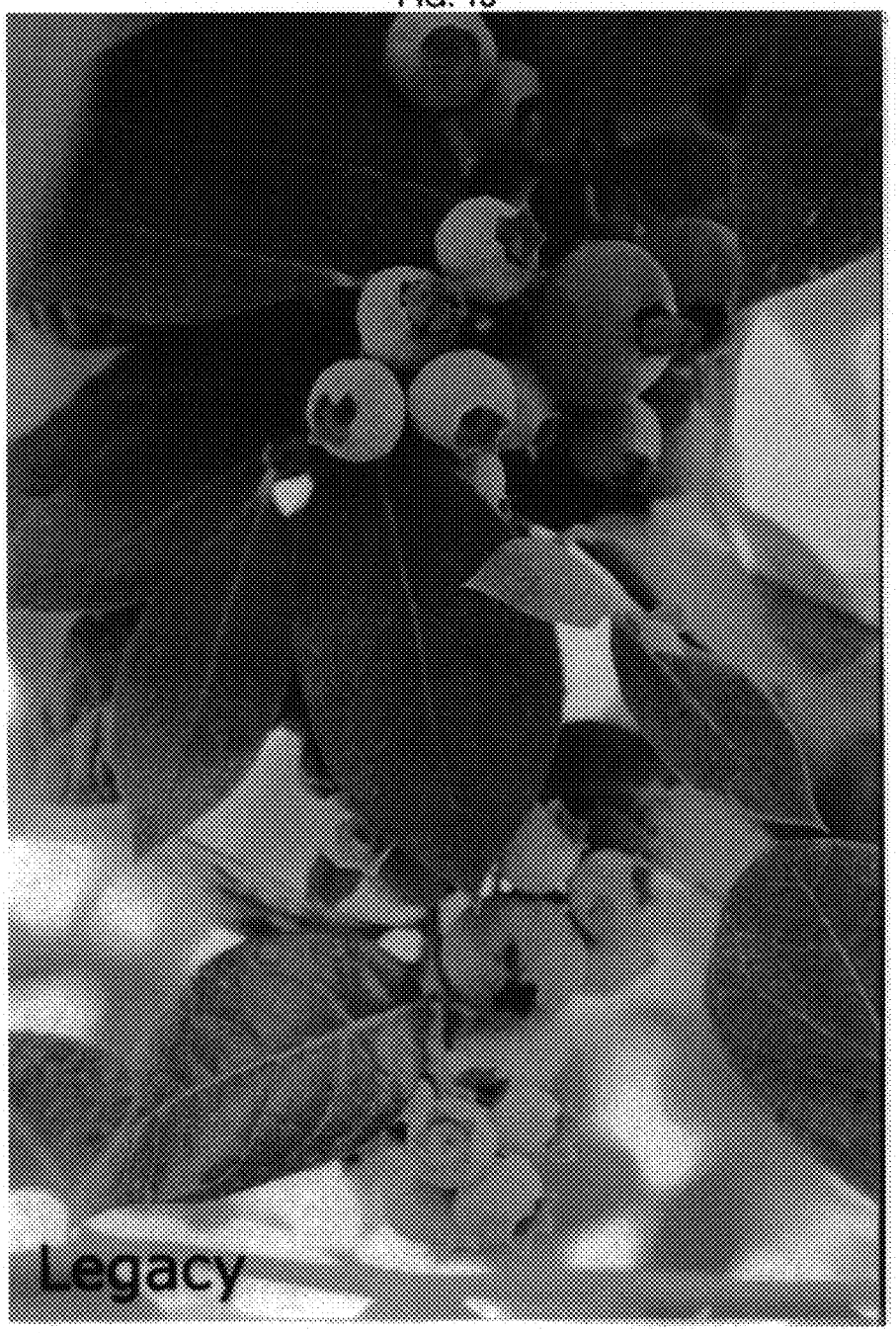
FIG. 15 shows the density of fruit cluster of 'Legacy' (unpatented) which is higher than density of fruit cluster of the new variety (designated 15.07.005).
Figure 16:
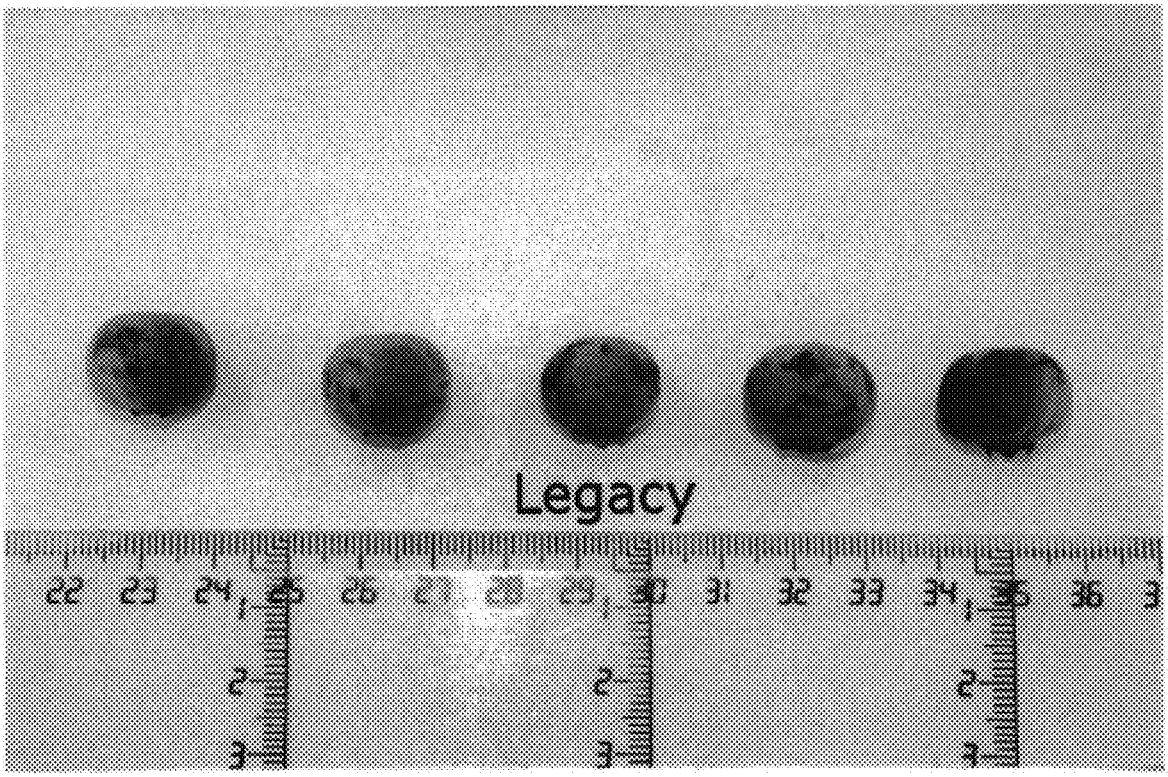
FIG. 16 shows the fruit of blueberry variety 'Legacy' (unpatented) which exhibits a fruit size smaller than the fruit of the new variety (designated 15.07.005).
Figure 17:
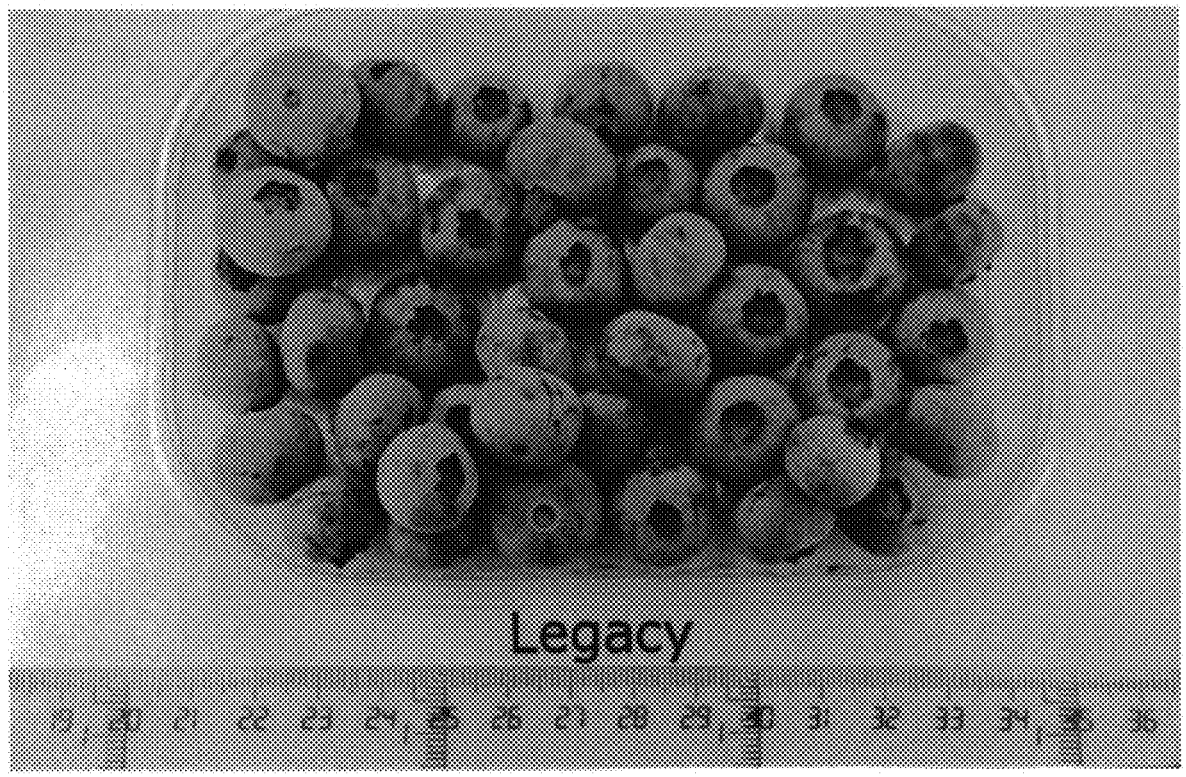
FIG. 17 shows several fruits of blueberry variety 'Legacy' (unpatented) which exhibits a medium depth of calyx basin.

The following detailed description of the new variety is based upon observations taken of plants and fruits grown "underglass", i.e. undertunnel, in the farm in Cartaya (Huelva), Spain, 7° W., 37° N., 45 feet elevation.

The following description is in accordance with UPOV terminology and the color teminology herein is in accordance with The Royal Horticultural Society Colour Chart (R.H.S.C.C.), 3$^{rd}$ edition published in 1995. The color descriptions and other phenotypical descriptions may deviate from the stated values and descriptions depending upon variation in environmental, seasonal, climatic and cultural conditions.

PROPAGATION

The new variety is principally propagated by softwood cuttings. Although propagation by softwood cuttings is presently preferred, other know methods of propagating blueberry plants may be used.

Blueberry root and develop well after transplanting.

GENERAL

'Plablue 1525' is propagated by softwood cuttings. It is a variety with fruit production from beginning March through ending May. It is a self-fertile variety. It produces large quantities of pollen throughout the seasons and pollination is good.

Production: Plants described are from high elevation nursery in Segovia, Spain, 3° 59' W., 41° 22' N., 2742 feet elevation.

Trials pursued in Cartaya (Huelva), Spain.

Date of planting: 14th October.

Number of repetitions: 2

Plants per repetition: 50

TABLE 1

Table 1 shows the accumulated production of fruit (g/plant) of the new variety 'Plablue 1525' when compared to its closest varieties 'Legacy' and 'Star'.

| Variety | March 31 | April 30 | June 22 |
|---|---|---|---|
| Plablue 1525 | 1093.00 | 2121.00 | 4224.00 |
| Legacy | 0.00 | 71.33 | 4998.00 |
| Star | 757.65 | 1781.73 | 1803.10 |

TABLE 2

Table 2 shows the weight (g/fruit) at three dates of the new variety 'Plablue 1502' when compared to its closest varieties 'Legacy' and 'Star'.

| Variety | March 31 | April 30 | June 22 |
|---|---|---|---|
| Plablue 1525 | 20.00 | 20.00 | 18.00 |
| Legacy | 0.00 | 17.00 | 16.00 |
| Star | 18.00 | 18.00 | 17.00 |

**Weight is shown as the average weight per fruit

DETAILED DESCRIPTION OF THE NEW VARIETY

The following additional information is provided to further describe the new variety.

Variety: 'Plablue 1525'. Breeder Ref. 15.07.005.

Latin name: *Vaccinium corymbosum* L.

Common name: Southern highbush blueberry.

Plants are growing in containers of 45 liters of capacity.

Plant:

*Habit*.—Semi-upright.

*Vigor*.—Medium.

*Height of plant*.—About 1.70 m.

*Canopy diameter*.—About 1.50 m.

*Twigginess*.—High.

*Suckering*.—Medium.

*Evergreenness*.—Evergreen.

*Chilling requirement*.—Approximately 200-400 hour at temperatures at or below 7° C.

*Cold hardiness*.—Has not been grown in all environments including harsh winter environments. Cold tolerance is expected to be low-mid.

Trunk and branches:

*Surface texture new wood*.—Smooth.

*Surface texture* 1 *year wood*.—Smooth.

*Surface texture* 2 *years and older wood*.—Rough.

*Diameter new wood*.—About 5.0 to 5.5 mm.

*Diameter* 1 *year wood*.—About 7.0 to 8.0 mm.

*Diameter* 2 *years old wood*.—About 17.0 to 18.0 mm.

*Color*.—New wood about yellow-green color (RHS Yellow-Green group color near 144 C to 144 B) transitioning to about greyed-orange color (RHS Greyed-Orange group color near 177 C to 177 A) in about 2 year old wood.

Leaf:

*Internode length*.—About 15.1 to 19.3 mm.

*Leaf arrangement*.—Alternate simple.

*Length*.—About 8.5 to 9.3 cm.

*Width*.—About 3.9 to 4.1 cm.

*Leaf shape*.—Lanceolate.

*Shape of tip*.—Acute.

*Shape of base*.—Acute.

*Shape of margin*.—Serrate.

*Venation pattern*.—Entire.

*Mature leaf color upperside*.—RHS green group near 139 B to 139 A.

*Mature leaf color underside*.—RHS green group color near 138 C to 138 B.

*Pubescence upper leaf surface*.—Absent.

*Pubescence under leaf surface*.—Absent.

*Pubescence leaf margin*.—Absent.

*Precocity*.—New vegetative growth before flowering.

Petiole:

*Length*.—About 3.0 to 3.5 mm.

*Width* (*diameter*).—About 1.9 to 2.3 mm.

*Texture*.—Smooth.

*Color*.—RHS Yellow-Green group color near 144 C to 144 B.

Flower:

*Flower arrangement*.—Compound raceme. Clusters at the end of branches.

*Flower shape*.—Rounded to slightly urceolate.

*Flowers per cluster*.—About 8 to 9.

*Flower fragrance*.—Faint. Sweet.

*Immature flower color*.—RHS Yellow-Green group color near 145 D to 145 C.

*Corolla*.—Length: About 9.0 to 9.5 mm. Diameter: About 9.0 to 10.0 mm. Aperture width: About 4.5 to 5.5 mm. Color: RHS White group color near 155 B to 155 A. Texture: Smooth.

*Peduncle*.—Length: About 12.0 to 13.0 mm. Color: RHS Yellow-Green group color near 144 C to 144 B.

*Pedicel*.—Length: About 9.0 to 10.0 mm. Color: RHS Yellow-Green group color near 144 C to 144 B. Calyx (with sepals) Diameter: About 9.5 to 10.5 mm. Calyx texture: Smooth. Color center of calyx: RHS Yellow-Green group color near 146 D to 146 C. Color sepals: RHS Yellow-Green group color near 144 D to 144 C. Attitude of sepals: Erect. Type of sepals: Reflexed.

*Stamen*.—Length: About 5.5 to 6.0 mm. Number per flower: About 11 to 13. Filament color: RHS Yellow-Green group color near 145 D to 145 C.

*Style*.—Length: About 6.9 to 7.2 mm. Color: RHS Green group color near 142 C to 142 B.

*Pistil*.—Length: About 8.3 to 8.8 mm. Ovary color: RHS Yellow-Green group color near 145 D to 145 C.

*Anther*.—Length: About 2.5 to 3.0 mm. Number: About 11 to 13. Color: RHS Greyed-Orange group color near 166 C to 166 B.

*Pollen*.—Abundance: Medium. Color: RHS Yellow-Orange group color near 20 C to 20 B.

*Self-compatibility*.—The cultivar has demonstrated a high degree of self-compatibility.

Fruit:

*Fruiting type*.—On one-year-old and current season's shoots.

*Calyx aperture*.—About 9.0 to 11.0 mm.

*Calyx lobes*.—About 6 to 8 lobes.

*Calyx depth*.—About 1.7 to 2.0 mm.

*Pedicel length*.—About 9.5 to 10.0 mm.

*Pedicel surface texture*.—Smooth.

*Peduncle length*.—About 12.0 to 13.0 mm.

*Peduncle surface texture*.—Smooth.

*Berries per cluster*.—About 8 to 9.

*Berry detachment*.—Easy.

*Weight*.—About 18 to 20 grs.

*Height*.—About 14.0 to 16.0 mm.

*Width*.—About 18.5 to 21.0 mm.

*Shape*.—Oblate.

*Color with wax*.—RHS Violet-Blue group color near 97 C to 97 D.

*Color with wax removed*.—RHS Black group color near 202 A.

*Wax*.—Persistent wax.

*Surface wax abundance*.—Moderate.

*Flesh color*.—RHS Yellow-Green group color near 149 D to 150 D.

*Pedicel scar*.—About 0.9 to 1.3 mm.

*Firmness*.—Moderate firm.

*Texture*.—Creamy.

Seed:

*Color*.—RHS Greyed-Orange group color near 165 B to 165 A.

*Length*.—About 1.5 to 2.0 mm.

*Width*.—About 0.95 to 1.0 mm.

*Weight*.—About 0.3 to 0.4 mg.

*Seeds per berry*.—About 12 to 14.

General: The growing period in Huelva, Spain, where the observations on primocane production were made, is between about November 20 and June 22 of the following year. 'Plablue 1525' is a blueberry variety that benefits from induction to flowering by low-mid chilling, about 200-400 hours are sufficient, preferably at temperatures of 7° C. or less. Normally, the minimum number of hours is accumulated in the field during several days. 'Plablue 1525' is a variety with consistent fruit production beginning in the first days of March and ending at the end of May. After planting as aforesaid, plants are grown in containers under tunnel. Water and fertilizer were applied through drip irrigation.

Date of planting: About October 15 in the farm, in Cartaya (Huelva), Spain, about 7° W, 37° N, 45 feet elevation. Time of flowering data: 10% flowering on primocane occurs about November 30. First mature fruits are about March 1 (15-20 g/plant), with a maximum production at the middle of May.

Storage qualities: 'Plablue 1525' fruit maintain their quality characteristics when kept in a frigo chamber at temperatures of about 2° C. for about 22 days. The fruit's color remains substantially the same. Shelf life of 'Plablue 1525' is good.

Use/market: The berries of 'Plablue 1525' are suitable for consumption as fresh fruit. Also, they are amenable to processing.

Disease resistance: No particular sensitivity to any disease or pest has been observed for 'Plablue 1525'

I claim:

1. A new and distinct blueberry plant of the variety substantially as shown and described.

* * * * *